US011317849B2

(12) United States Patent
Na et al.

(10) Patent No.: US 11,317,849 B2
(45) Date of Patent: May 3, 2022

(54) VIRTUAL REALITY DEVICE FOR DIAGNOSIS OF NERVE DISORDER, SYSTEM AND METHOD FOR THEREOF

(71) Applicants: Samsung Life Public Welfare Foundation, Seoul (KR); Korea Institute of Science and Technology, Seoul (KR)

(72) Inventors: Duk Lyul Na, Seoul (KR); Ko Woon Kim, Seoul (KR); Jong Doo Choi, Seoul (KR); Ju Hee Chin, Seongnam-si (KR); Byung Hwa Lee, Anyang-si (KR); Jee Hyun Choi, Seoul (KR); Hye Joo Lee, Seongnam-si (KR); Hyo Been Han, Gimpo-si (KR)

(73) Assignees: Samsung Life Public of Welfare Foundation, Seoul (KR); Korea Institute of Science and Technology, Seoul (KR)

(*) Notice: Subject to any disclaimer, the term of this patent is extended or adjusted under 35 U.S.C. 154(b) by 778 days.

(21) Appl. No.: 16/131,269

(22) Filed: Sep. 14, 2018

(65) Prior Publication Data

US 2019/0090802 A1 Mar. 28, 2019

(30) Foreign Application Priority Data

Sep. 27, 2017 (KR) .......................... 10-2017-0124778

(51) Int. Cl.
| | |
|---|---|
| *A61B 5/00* | (2006.01) |
| *G09B 7/02* | (2006.01) |
| *G06T 19/00* | (2011.01) |
| *G02B 27/01* | (2006.01) |
| *G09B 23/28* | (2006.01) |
| *G06F 3/01* | (2006.01) |

(52) U.S. Cl.
CPC .......... *A61B 5/4076* (2013.01); *A61B 5/4088* (2013.01); *G02B 27/017* (2013.01); *G06F 3/011* (2013.01); *G06T 19/006* (2013.01); *G09B 7/02* (2013.01); *G09B 23/28* (2013.01); *A61B 2562/0204* (2013.01)

(58) Field of Classification Search
CPC combination set(s) only.
See application file for complete search history.

(56) References Cited

U.S. PATENT DOCUMENTS 9,251,713 B1* 2/2016 Giovanniello ......... G16H 50/20
2007/0027406 A1* 2/2007 LaPlaca ............... A61B 5/4076
600/558

(Continued)

OTHER PUBLICATIONS

Pugnetti et al. Evaluation and Retraining of Adults' Cognitive Impairments: Which Role for Virtual Reality Technology? Comput. Biol. Med. vol. 25, No. 2, pp. 213-227, 1995. (Year: 1995).*

(Continued)

*Primary Examiner* — Etsub D Berhanu
(74) *Attorney, Agent, or Firm* — Rabin & Berdo, P.C.

(57) ABSTRACT

Disclosed is a VR (Virtual Reality) device for diagnosis of nerve disorder, system and method thereof, wherein the device comprises: a display part providing a user with a VR environment in response to an image; and a user response receiver receiving a user response relative to the image, and wherein the image includes an introduction video included with two or more characters, and a question video image provided subsequent to the introduction video to include an inquiry related to the characters, whereby a user's linguistic competence, visual ability and associative ability can be comprehensively evaluated, and more accurately grasp a degree of user's nerve disorder can be accurately grasped without being influenced by a user's academic background and age.

10 Claims, 11 Drawing Sheets

(56) References Cited

U.S. PATENT DOCUMENTS

2016/0378177 A1* 12/2016 Wei .................. G06F 3/012
                                                   345/156
2017/0285737 A1* 10/2017 Khalid ............... G06F 3/011

OTHER PUBLICATIONS

Rose et al. Virtual Environments in Neuropsychological Assesment and Rehabilitation. Virtual Reality in Neuro-Psycho-Physiology, 1997. (Year: 1997).*
Baek et al. The usefulness of the story recall test in patients with mild cognitive impairment and Alzheimer's disease. Aging Neuropsychology and Cognition, Mar. 2011. (Year: 2011).*
Rizzo et al. Virtual Reality and Cognitive Assessment and Rehabilitation: The State of the Art. Virtual Reality in Neuro-Psycho-Physiology, 1997. (Year: 1997).*
Attree et al. Virtual Environments in Neuropsychological Assessment and Rehabilitation. Studies in Health Technology and Informatics. Feb. 1997. (Year: 1997).*
Garcia-Betances et al. A succinct overview of virtual reality technology use in Alzheimer's disease. Frontiers in Aging Neuroscience. 2015. (Year: 2015).*
Manera et al. A Feasibility Study with Image-Based Rendered Virtual Reality in Patients with Mild Cognitive Impairment and Dementia. 2016. (Year: 2016).*

* cited by examiner

It is a question to a person sitting on a red circle.

1. What is your name?
2. What is your occupation?
3. What is your hobby?
4. What is your relationship with the main character?
5. What kind of present did you give?
6. Where is your living area?

Faces of persons are to appear on a screen one by one. The subject is to guess if the face of the person is the one who appeared on the video.

1. If the face is the one who has appeared on the video, check on O

2. If the face is not the one who has appeared on the video, check on X

Has the person on the photograph appeared on the video?
FIG. 4

This is a step evaluating how well you remember the content introduced in the video. The example includes a total of six and you are requested to press one of the numbers of 1~6 corresponding to a correct answer.
FIG. 5
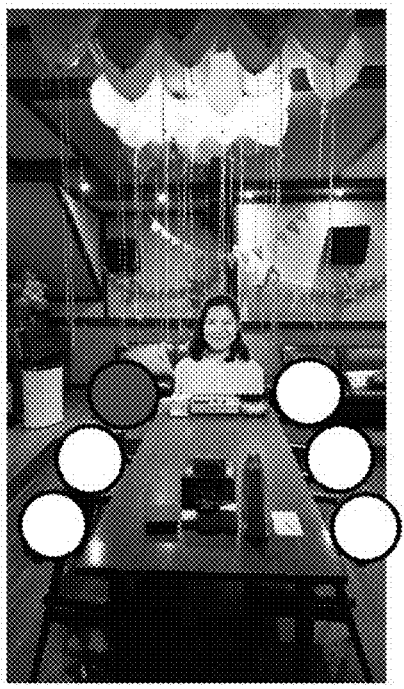
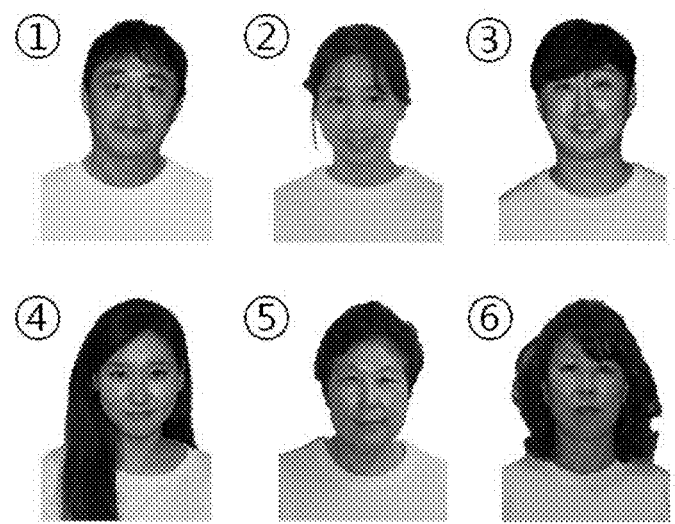
FIG. 6

ACTOR AND NON-ACTOR TO BE MATCHED ACCORDING TO AGE AND GENDER
- ACTORS (3 MALES, 3 FEMALES/40s ~ 50s: 4 PERSONS, 20s ~ 30s: 3 PERSONS)
- NON-ACTORS (6 MALES, 6 FEMALES/40s ~ 50s: 6 PERSONS, 20s ~ 30s: 6 PERSONS)

| 1. FLOWER POT | 2. AIRPLANE TICKET | 3. PURSE | 4. COSMETICS | 5. HAIR PIN | 6. WRIST WATCH |
|---|---|---|---|---|---|
| 7. CUP | 8. CHOCOLATE | 9. NECKLACE | 10. FLOWER | 11. MOBILE PHONE CASE | 12. KEY CHAIN |
| 13. BAG | 14. SHOES | 15. DOLL | 16. CLOTHES | 17. GUITAR | 18. PERFUME |

FIG. 8

| 1. SCARF | 2. HAT | 3. GLASSES | 4. NECKTIE | 5. HAIR BAND | 6. SUN GLASSES |
|---|---|---|---|---|---|
| 7. HEAD BAND | 8. WIG | 9. MUFFLER | 10. FUR HAT | 11. MASK | 12. BROOCH |
| 13. BEANIE CAP | 14. RING | 15. BOW TIE | 16. BRACELET | 17. BOWLER | 18. EAR RING |

FIG. 9

| NAME | OCCUPATION | HOBBY | AREA | RELATION |
|---|---|---|---|---|
| 1. Kim, seun-young | 1. BANK TELLER | 1. ORCHID PLANTING | 1. SEOUL | 1. MOMMY FRIEND |
| 2. Lee, young-ho | 2. AIRPLANE PILOT | 2. PHOTO SHOOTING | 2. INCHEON | 2. EXTRACURRICULUM TEACHER |
| 3. Cho, mi-gyung | 3. MEDICAL DOCTOR | 3. GUITAR PLAYING | 3. DAEGU | 3. SISTER AT MUSIC INSTITUTE |
| 4. Lee, young-ho | 4. SINGER | 4. COOKING | 4. GWANGJU | 4. SENIOR AT HIGH SCHOOL |
| 5. Chung, eun-gyung | 5. PAINTER | 5. BOXING | 5. BUSAN | 5. JUNIOR COUSIN |
| 6. Kang, jun-ho | 6. HIGH SCHOOL TEACHER | 6. OVERSEAS TRIP | 6. DAEJON | 6. FRIEND AT ELEMENTARY SCHOOL |
| 7. Park, hae-sun | 7. ATTORNEY AT LAW | 7. MOVIE WATCHING | 7. ULSAN | 7. UNCLE |
| 8. Lee, ji-woo | 8. NURSE | 8. BOOK READING | 8. SUWON | 8. AUNT |
| 9. Choi, ji-hae | 9. POLICE MAN | 9. STROLLING | 9. JEJUDO | 9. NEPHEW |
| 10. Cho, ji-eun | 10. CIVIL SERVANT | 10. SWIMMING | 10. CHANGWON | 10. LOVER |
| 11. Kang, yun-yon-ah | 11. FIRE FIGHTER | 11. TV WATCHING | 11. JEONJU | 11. JUNIOR AT CIRCLE |
| 12. Kim, su-youn | 12. PROFESSOR | 12. KNITTING | 12. POHANG | 12. UNIVERSITY PROFESSOR |
| 13. Park, ji-ho | 13. ATHLETE | 13. MUSIC LISTENING | 13. CHUNAN | 13. DOCTOR'S COMPANION |
| 14. Lee, min-jung | 14. COMPANY EMPLOYEE | 14. PINGPONG GAME | 14. CHUNGJU | 14. NEIGHBOR |
| 15. Choi, jung-hwan | 15. RESEARCHER | 15. MOUNTAIN CLIMBING | 15. WONJU | 15. BROTHER AT CHURCH |
| 16. Han, ju-hyung | 16. ACTOR | 16. FISHING | 16. CHUNGCHUN | 16. FATHER'S SISTER |
| 17. Chung, hyun-su | 17. BUS DRIVER | 17. COMPUTER GAME | 17. GIMJAE | 17. MALE INTRODUCED FROM A BLIND DATE |
| 18. Kim, dong-young | 18. SINGER | 18. ORGANIZING | 18. GUMI | 18. MAN AT THE JOURNEY |

FIG. 10

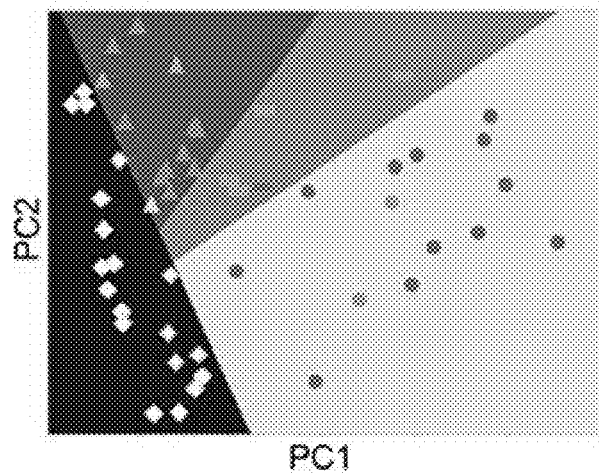
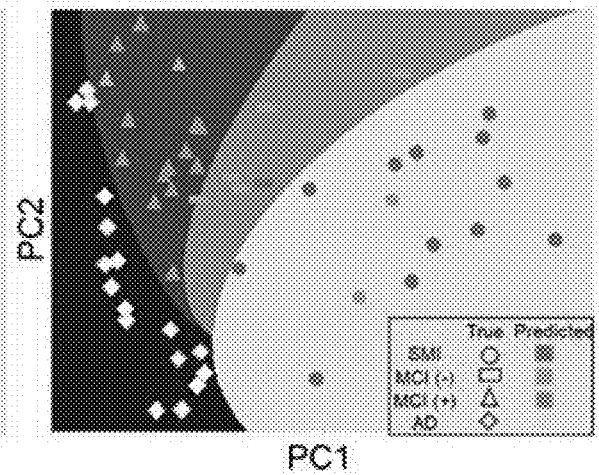
FIG. 12A  FIG. 12B
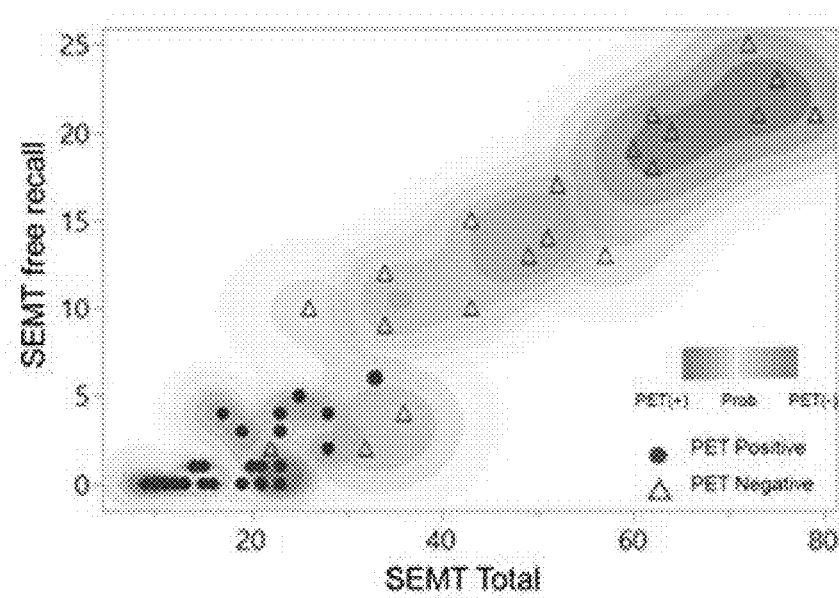
FIG. 13

VIRTUAL REALITY DEVICE FOR DIAGNOSIS OF NERVE DISORDER, SYSTEM AND METHOD FOR THEREOF

TECHNICAL FIELD

The present invention relates to a VR (Virtual Reality) device for diagnosis of nerve disorder, system and method thereof using VR, and more particularly, to a VR device for diagnosis of nerve disorder and system configured to comprehensively evaluate a user's linguistic competence, visual ability and associative ability, and to more accurately grasp a degree of user's nerve disorder without being influenced by a user's academic background and age, and a method thereof.

BACKGROUND OF INVENTION

Ageing is rapidly being progressed world-wide, and the number of dementia patients is also greatly increased along with the phenomenon of worldwide ageing. As a result, economic costs to treat and manage the dementia patients are also increased. Recently, medications for delaying and improving the appearance of dementia symptoms have been developed, and particularly, investment and efforts to develop efficacy-further improved medications are being continuously waged. However, these medications are efficacious when used at an initial stage of dementia, such that it is important to diagnose and to treat the dementia at an early stage.

The conventional methods to diagnose the dementia may include a method of diagnosing the progressing degree of dementia by photographing brain image using MRI (Magnetic Resonance Imaging) equipment, a bio-marker method of diagnosing the progressing degree of dementia by analyzing blood or cerebrospinal fluid extracted from a dementia patient and a method of diagnosing the dementia by measuring brainwave (EEG or MEG). However, these methods suffer from disadvantages in that patients' cost-wise burdens are increased due to use of high-priced devices, and patients' pains are involved because blood or cerebrospinal fluid must be extracted from patients.

Meanwhile, a dementia diagnosis method is generally performed through psychological medical examination in order to diagnose the dementia. However, the dementia diagnosis method performed through psychological medical examination requires a long time of medical examination under an examination room environment which may provide a mental pressure or stress to a patient and may result in degradation in accuracy of tests. Furthermore, the medical examination test is performed in writing, which is a lengthy and rigid test, causing embarrassment to the patient and which can be difficult in being performed to the last minute due to weak test motivation. Furthermore, the written test is greatly affected by educations.

As a result, the thing is that a test is required that can reflect the cognitive performance process experienced by dementia patient in the everyday life.

DETAILED DESCRIPTION OF THE INVENTION

Technical Subject

The present invention is provided to solve the aforesaid problems, and it is an object of the present invention to provide a VR device for diagnosis of nerve disorder and system configured to comprehensively evaluate a user's linguistic competence, visual ability and associative ability based on actual everyday life, and a method thereof.

Furthermore, the present invention is to grasp a user's degree of nervous disorder more accurately because the present invention has a correlation meaningfully similar to the existing language memory test (SVLT: Seoul Verbal Learning Test) and can distinguish a difference in response to Beta amyloid positive/negative without recourse to influence of user's education and age differently from the existing simplified mental state examination (MMSE: Mini Mental State Examination).

Technical Solution

In one general aspect of the present invention, there is provided a VR device for diagnosis of nerve disorder, the device comprising: a display part providing a user with a VR environment in response to an image; and a user response receiver receiving a user response relative to the image, wherein the image includes an introduction video included with two or more characters, and a question video image provided subsequent to the introduction video to include an inquiry related to the characters.

Here, the display part may be an HMD (Head Mounted Display) including a display providing a VR environment.

Furthermore, the user response receiver may be a controller including a button part receiving a user response to the question video.

Furthermore, the present invention may further comprise a user response analyzer analyzing a user response received by the user response receiver and distinguishing the user in response to the analyzed user response.

Furthermore, the introduction video may preferably be a video photographed by a 360° camera.

Furthermore, the introduction video may be a birthday party video including one or more main characters and two or more congratulating persons, and preferably, the introduction video may be properly a video including one main character sitting at a table and six congratulating persons sitting around the main character.

Furthermore, the introduction video may include a content in which the congratulating persons introduce in sequence one or more contents selected from a group consisting of own name, an occupation, a hobby, relation with the main character, a present and an area.

Furthermore, the congratulating persons in the introduction video may preferably have one or more contents selected from a group consisting of mutually different genders, ages, accessories and clothes colors.

Furthermore, the question video may include one or more of videos including a recall video recalling the introduction video, a recognition video testing a memory to a face of the congratulating persons, and a matching video testing a memory relative to characteristics of the congratulating persons.

Furthermore, the question video may preferably include, in sequence, the recall video, the recognition video and the matching video.

Furthermore, the recall video may include a questionnaire questioning one or more contents selected from a group consisting of an image or explanation designating one person from the congratulating persons, name of the designated person, an occupation, a hobby, relation with the main character, a present and an area.

Furthermore, the recognition video may preferably include a face photograph of one person in the congratulating persons and a face photograph of a person not in the congratulating persons.

Furthermore, the recognition video may include, in a random order, a face photograph of one person in the congratulating persons and a face photograph of a person not in the congratulating persons, where the face photograph of one person in the congratulating persons and the face photograph of a person not in the congratulating persons are mutually distinguished.

Furthermore, the matching video may include: a questionnaire questioning one or more contents selected from a group consisting of an image or explanation designating one person from the congratulating persons, a face, a name of the designated person, an occupation, a hobby, relation with the main character, a present and an area; and one or more candidate answers selected from a group consisting of a face, a name, a hobby of congratulating person, a relation with the main character, a present and an area.

Furthermore, the user response receiver may preferably score a user's correct rate based on a response received from the user.

Furthermore, the user response receiver may preferably determine a user's dementia progress degree based on the scored grade.

Meantime, in another general aspect of the present invention, there is provided a VR system for diagnosis of nerve disorder, comprising: a VR device; and a server analyzing a user response received from a user response receiver of the VR device and classifying a user according to the analyzed user response.

In addition, in still another general aspect of the present invention, there is provided a method for VR device for diagnosis of nerve disorder, the method comprising: providing a VR environment to a user through a display in response to a video; and receiving a user response relative to the video, wherein the video includes an introduction video including two or more characters, and a question video provided subsequent to the introduction video to include a question related to the characters.

Advantageous Effects

The present invention has advantageous effects in that a VR of a video can be provided to a user, and the video includes an introduction video including two or more characters and a question video including questions related to the characters, whereby a user's linguistic competence, visual ability and associative ability can be comprehensively evaluated.

Furthermore, the present invention has advantageous effects in that a user's degree of nervous disorder can be grasped more accurately because the present invention has a correlation meaningfully similar to the existing language memory test (SVLT: Seoul Verbal Learning Test) and can distinguish a difference in response to Beta amyloid positive/negative without recourse to influence of user's education and age differently from the existing the MMSE (Mini Mental State Examination).

BRIEF DESCRIPTION OF DRAWINGS

FIG. 4 is a photograph illustrating an example of a recognition video in a question video according to the present invention.

FIG. 5 is a photograph illustrating an example in order to explain a matching video in a question video according to the present invention.

FIG. 6 is a photograph illustrating an example of a matching video in a question video according to the present invention.

FIG. 8 is a photograph illustrating an example of a present questionnaire in a matching video of a question video according to the present invention.

FIG. 9 is a photograph illustrating an example of an accessory questionnaire in a matching video in a question video according to the present invention.

FIG. 10 is a mimetic diagram illustrating an example of a questionnaire for name, occupation, area and relation of a matching video in a question video according to the present invention.

FIGS. 12A and 12B are graphs of a PC (Principal Component) result certifying whether four groups (SCI, aMCI(-), aMCI(+), AD) are well classified by a classifier using scores of SEMT according to an exemplary embodiment of the present invention. FIGS. 12A and 12B are results where patient groups of same data are classified by two different PCs (Principal Components), where FIG. 12A is a linear kernel, and FIG. 12B is a radial kernel.

FIG. 13 is a picture of a result of scores of SEMT predicted in a probability value between 0 and 1 in response to presence/absence of amyloid deposition using a regression analysis method (Rogistic regression model) according to an exemplary embodiment of the present invention.

BEST MODE

Figure 1:
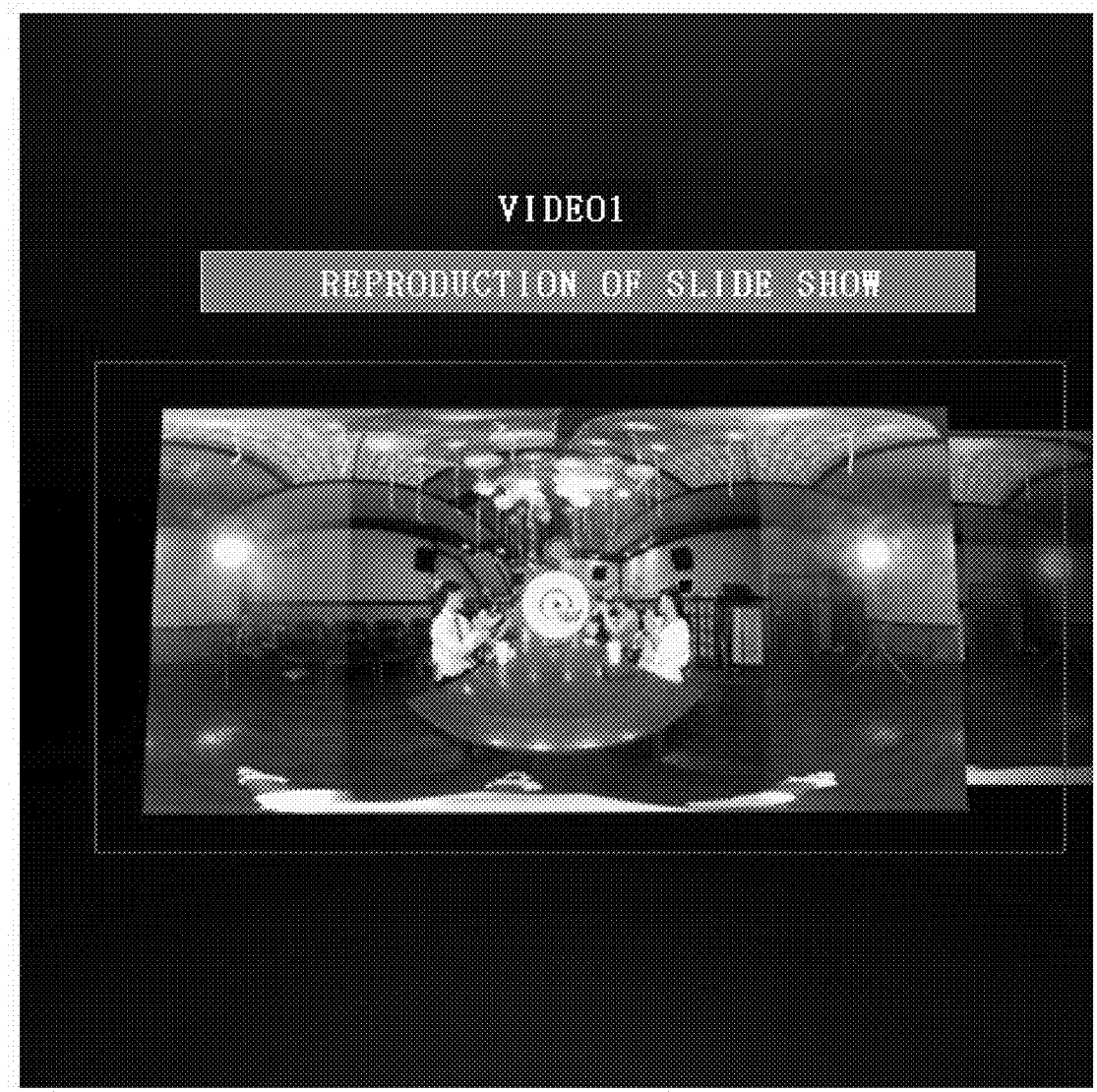
FIG. 1 is a photograph illustrating an example of a VR in order to explain an introduction video according to the present invention.

The present invention may have various exemplary embodiments while being applied with various changes, and is intended to exemplify specific exemplary embodiments with reference to drawings and to explain in detail the exemplary embodiments in the Detailed Description. The embodiments are, however, intended to be illustrative only, and thereby do not limit the scope of protection of the present invention. Thereby, it should be appreciated that numerous other changes, equivalents, modifications and embodiments can be devised that will fall within the spirit and scope of the principles of this invention. In describing the present invention, detailed descriptions of constructions or processes known in the art may be omitted to avoid obscuring appreciation of the invention by a person of ordinary skill in the art with unnecessary detail regarding such known constructions and functions Terms used in the specification are only provided to illustrate the embodiments and should not be construed as limiting the scope and spirit of the present invention. In the specification, a singular form of terms includes plural forms thereof, unless specifically mentioned otherwise. In the term "includes", "including", "comprises" and/or "comprising" as used herein, the mentioned component, step, operation and/or device is not excluded from presence or addition of one or more other components, steps, operations and/or devices. The present invention may have various exemplary embodiments while being applied with various changes, and is intended to exemplify specific exemplary embodiments with reference to drawings and to explain in detail the exemplary embodiments in the Detailed Description. The embodiments are, however, intended to be illustrative only, and thereby do not limit the scope of protection of the present invention. Thereby, it should be appreciated that numerous other changes, equivalents, modifications and embodiments can be devised that will fall within the spirit and scope of the principles of this invention. In describing the present invention, detailed descriptions of constructions or processes known in the art may be omitted to avoid obscuring appreciation of the invention by a person of ordinary skill in the art with unnecessary detail regarding such known constructions and functions Terms used in the specification are only provided to illustrate the embodiments and should not be construed as limiting the scope and spirit of the present invention. In the specification, a singular form of terms includes plural forms thereof, unless specifically mentioned otherwise. In the term "includes", "including", "comprises" and/or "comprising" as used herein, the mentioned component, step, operation and/or device is not excluded from presence or addition of one or more other components, steps, operations and/or devices.

The "nerve disorder" in the present specification means a nervous degenerative disorder, and may be selected from a group consisting of, for example, ADs (Alzheimer's Diseases), vascular dementia, FTDs (Frontal Lobe Dementia), CBDs (cortical retreat), PSPs (Proactive nuclear paralysis), dementia with Lewy bodies, tangle predominant senile dementia, PiDs (Pick's Diseases), argyrophilic grain disorders, ALSs (muscular dorsal sclerosis), other motor neurological disorders, Guam parkinson's disease-dementia-complexities, FTDP-17, Lytico-Bodig diseases, multiple sclerosis, TBI and parkinson's diseases. Although Alzheimer's diseases are exemplified in the following explanation, the present invention is not limited thereto.

A VR (Virtual Reality) device for diagnosis of nerve disorder according to an exemplary embodiment of the present invention may include a display part and a user response receiver.

The display part may provide a user with a VR environment in response to a video. The display part may be an HMD (Head Mounted Display) including a display providing a VR environment. Thus, the VR device according to the present invention may be a display device worn on a user head to directly display a video in front of a user's eyes. For example, the VR device may be formed with a wearable glass or an HMD (Head Mount Display). The VR device may take a shape of a pair of glasses, or may include a transparent or opaque display. As a result, the VR device may allow a user wearing the VR device to recognize as if he or she is in a VR space. The VR device according to an exemplary embodiment of the present invention may further include a display to allow a user to experience a VR, a speaker, a microphone or an operation detection sensor.

The user response receiver may receive a user response to a video provided by the display part. When a question video is provided to a user through the video, the user may respond thereto, and receive a response signal. The user response receiver may be a controller including a button part receiving a user response to the question video. Furthermore, the user response receiver may be included in the VR device according to the present invention, a display part or an HMD, or may be mounted thereon, and may be mounted separately (for example, may be included in a separate server).

A video provided by the display part in the VR device according to the present invention may be characterized by including an introduction video and a question video for diagnosing a nerve disorder. That is, the video may include an introduction video including two or more characters and a question video provided subsequent to the introduction video to include the characters and questions related thereto.

Because the video is provided to a user through a VR (Virtual Reality), a user' sense of reality and immersion degree can be increased whereby a user's progress in nerve disease can be more accurately determined.

FIG. 1 is a photograph illustrating an example of a VR in order to explain an introduction video according to the present invention, where as shown in FIG. 1, the video or the introduction video is preferably photographed by a 360 degree camera, and in this case, there is an effect of providing a feeling that a user is actually included in the video.

The introduction video includes two or more characters. The introduction video may function as a passage of a question for diagnosis of nerve disorder, through which a user's auditory or linguistic ability can be tested. Among other things, the introduction video included with characters has an advantageous effect of reflecting a recognition performance process familiar to a user and experienced by a dementia patient in everyday life by making a problem of a person contacted by all users. Furthermore, a level of difficulty in test may be adjusted by allowing characters to appear with two or more persons.

For example, the introduction video may be a birthday party video including one or more main characters and two or more congratulating characters. The birthday party may be applicable to all users, and a form of party may have an effect of increasing a user immersion degree. Furthermore, it may be proper that the introduction video be a birthday party video including one main character sitting at a table and six congratulating persons sitting around the main character (See FIG. 1) There may be a disadvantage of increasing complexity and confusion when characters continuously move, roam around or stand in the video. When one main character sits at a center of a table and six congratulating persons sit respectively at a designated place around the main character, there is an effect in that a user can remember focused on the positions of the characters, and various questions can be created about the positions of the characters.

In addition, the introduction video may include a content in which the congratulating persons introduce in sequence one or more contents selected from a group consisting of own name, an occupation, a hobby, relation with the main character, a present and an area. That is, the congratulating persons may unaffectedly, like naturally talking, talk about his or her own name, occupation, hobby, relation with the main character, present and/or area in which he or she lives.

Furthermore, the congratulating persons in the introduction video may preferably be one or more persons selected from a group consisting of persons of different gender, ages, and persons having different accessories and colors. That is, two or more congratulating persons may include persons of different gender, different ages and persons wearing different accessories and different colors of clothes.

For example, the congratulating persons may have basic information as shown in the following Table 1.

TABLE 1

| | classification | name | living place | occupation | accessories | ages | genders | presents | Colors of clothes |
|---|---|---|---|---|---|---|---|---|---|
| 1 | Main character | Park, cho-seo | | | | | F | | |
| 2 | Congratulating persons | Chung, eun-young | Busan | painter | headband | 20s | F | Head band | khaki |
| 3 | Congratulating persons | Kang, jun-ho | Daejon | teacher | sunglasses | 30s | M | Wrist watch | blue |
| 4 | Congratulating persons | Cho, mi-gyung | Daegu | Medical doctor | glasses | 40s | F | purse | white |
| 5 | Congratulating persons | Lee, young-ho | Gwang ju | singer | necktie | 30s | M | cosmetics | yellow |
| 6 | Congratulating persons | Choi, min-hyuck | Incheon | Airplane pilot | hat | 40s | M | Airplane ticket | grey |
| 7 | Congratulating persons | Kim, sun-young | Seoul | Bank teller | scarf | 50s | F | Flower pot | black |

The congratulating persons may introduce, at one go, and at the time of introducing himself or herself, his or her name, occupation, hobby, relation with the main character, present and living area, and may introduce one at a time through a user conversation process with several other persons. The order in which the congratulating persons introduce himself or herself may be done based on designated positions, and may introduce himself or herself randomly regardless of sitting positions. The congratulating persons may implement the introduction about himself or herself according to a predetermined script including casual conversations. Through this process, it is preferable that the congratulating persons equally provide the information of repeatedly talking his or her information twice, whereby the information can be remembered by a user.

In contrast, it is preferable that the congratulating persons not talk about his or her gender, age, accessory and the color of clothes. This information may be provided through video. Thus, it is possible to evaluate a user's visual ability through this process.

The above question(ing) video is provided subsequent to introduction video, and may include a question related to the characters. The types or shapes of questions are not particularly limited. For example, the questions may include a name of congratulating person, occupation, hobby, relation with the main character, present and/or living area, and may include a question related to gender, age, accessory and/or clothes of congratulating persons. The question is also provided via video which can evaluate the user's visual ability and linguistic competence, and is preferable for quick evaluation. In addition thereto, it is also possible for the questioning video to further include an auditory sound element. The questioning video will be further explained in detail later.

The present invention may provide a user with a VR environment through a video, and may include an introduction video including two or more characters and a question video including a question related to the characters, whereby an advantageous effect of comprehensively evaluating a user's linguistic competence, visual ability and associative ability can be accomplished.

To be more specific, the question video may include one or more videos including a recall video recalling the introduction video, a recognition video testing a memory to a face of the congratulating persons, and a matching video testing a memory relative to characteristics of the congratulating persons.

The question video may preferably include in sequence the recall video, the recognition video and the matching video.

The recall video has a function of free-recalling by a user of content about the introduction video provided to the user, prior to start of a full-fledged question. Furthermore, the recognition video is to test the memory of a face that is first remembered basically by the user, and is provided prior to testing various detailed information or characteristics of congratulating persons, and may have an effect of testing the user's memory step by step. Successively, the matching video is an in-depth step testing a memory of detailed various information or characteristics of congratulating persons.

Figure 2:
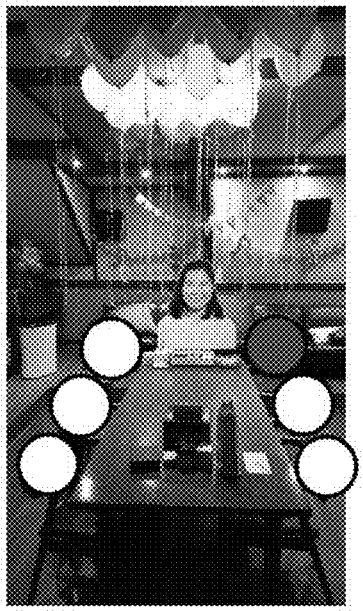
FIG. 2 is a photograph illustrating an example of a recall video in a question video according to the present invention.

FIG. 2 is a photograph illustrating an example of a recall video in a question video according to the present invention. As shown in FIG. 2, the recall video may include a questionnaire questioning one or more contents selected from a group consisting of an image and/or explanation designating one person from the congratulating persons, name of the designated person, an occupation, a hobby, relation with the main character, a present and an area. Two or more questions may be shown at one go in the questionnaire, and questions may be shown one by one in sequence. The questions in the step of recall may preferably not be too detailed or too specific and may preferably allow the congratulating persons to select to converse in oral manner in the introduction video.

For example, a screen as illustrated in FIG. 2 may be proposed to a user, and each question may be also provided in sound. Furthermore, it may be possible that a candidate answer to each question may be proposed as an example (or selection) to be provided as multiple choice questions. Then, the user may select an answer to each question or talk in voice to express a response.

Figure 3:
FIG. 3 is a photograph illustrating an example in order to explain a recognition video in a question video according to the present invention.

FIG. 3 is a photograph illustrating an example in order to explain a recognition video in a question video according to the present invention, and FIG. 4 is a photograph illustrating an example of a recognition video in a question video according to the present invention.

The recognition video is to test a memory of a face of a congratulating person. Furthermore, the recognition video may preferably include a test method, and a video or a screen explaining a user response method thereto. When only one face of a congratulating person is proposed in the recognition video, the user may be allowed to select O or X. To this end, the user may be preferably provided with a separate response means capable of selecting O or X.

Furthermore, the recognition video may allow to selectively include only one face photograph of one person in the congratulating persons or one face photograph of a person not in the congratulating persons, or may allow to include one face photograph or to include both face photographs on a screen. Preferably, inclusion in a random order of a face photograph of one person in the congratulating persons and a face photograph of a person not in the congratulating persons has an effect of testing the user response in the most simplified manner.

Furthermore, the recognition video may more preferably include, in a random order and in a mutually distinguishing manner, a face photograph of one person in the congratulating persons and a face photograph of a person not in the congratulating persons. For example, a total of 18 faces including six faces of congratulating persons and twelve faces of not congratulating persons are randomly shown to allow a user to response in a 0/X manner whether the face is the one shown in the introduction video.

Figure 7:
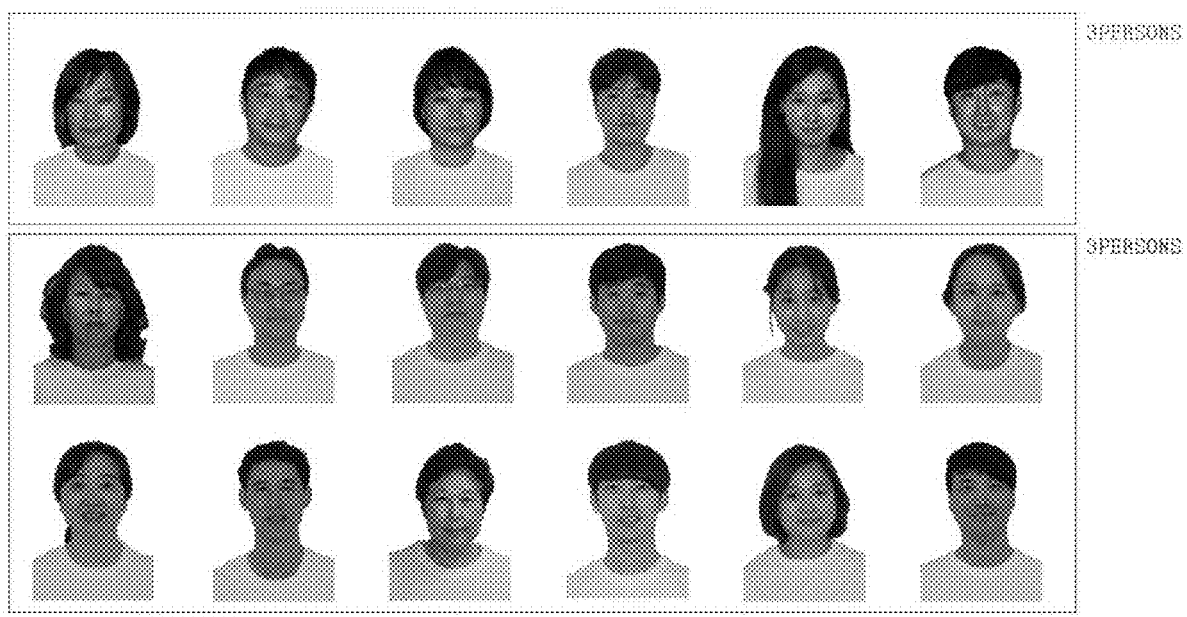
FIG. 7 is a photograph illustrating another example of a matching video in a question video according to the present invention.

FIG. 5 is a photograph illustrating an example in order to explain a matching video in a question video according to the present invention, FIG. 6 is a photograph illustrating an example of a matching video in a question video according to the present invention, and FIG. 7 is a photograph illustrating another example of a matching video in a question video according to the present invention.

The matching video is to test a memory of various detailed information or characteristics of congratulating persons. That is, the matching video is to evaluate how a user can well remember the contents introduced in the introduction video. Toward this end, the matching video may preferably include a video or a screen for a test method and a user response method thereto. When a plurality of faces, that is, two or more faces of congratulating persons and two or more faces of non-congratulating persons are simultaneously proposed, the user may select a number matching thereto (e.g., selecting 1 from 1~6). The matching video may be differentiated from the recognition video in that when a user face is proposed in the matching video, a plurality of faces, that is, two or more than two faces may be proposed at one go, or a position of congratulating person may be specified. The matching video may be advantageous in that a user's visual ability and associative ability can be simultaneously tested.

For example, as illustrated in FIG. 6, the matching video may include: a questionnaire questioning one or more contents selected from a group consisting of an image or explanation designating one person from the congratulating persons, a face, a name of the designated person, an occupation, a hobby, relation with the main character, a present and an area; and one or more candidate answers selected from a group consisting of a face, a name, a hobby of congratulating person, a relation with the main character, a present and an area.

Furthermore, as illustrated in FIG. 7, the candidate answer may include, as a selection, a total of six candidate answers in which three faces of congratulating persons (actors or actresses) and three faces of non-congratulating persons (non-actors or non-actresses). That is, a six-question multiple choice may be most effective for a user's memory test and a user response reception.

FIG. 8 is a photograph illustrating an example of a present questionnaire in a matching video of a question video according to the present invention, FIG. 9 is a photograph illustrating an example of an accessory questionnaire in a matching video in a question video according to the present invention, and FIG. 10 is a mimetic diagram illustrating an example of a questionnaire for name, occupation, area and relation of a matching video in a question video according to the present invention.

As illustrated in drawings, the questions in the matching video may include a name of congratulating person, occupation, relation with the main character, present and/or area, and may also include a face of congratulating person, a present and an accessory.

For example, a present questionnaire may be formed with a 6-question multiple choice question in which, among 18 presents, three presents prepared by the congratulating persons, and three presents prepared by the non-congratulating persons are combined from 18 presents as illustrated in FIG. 8. Furthermore, as illustrated in FIG. 9, a 6-question multiple choice question may be formed in which three accessories among the six accessories worn by the congratulating persons and three accessories among the twelve accessories worn by non-congratulating persons are combined.

This method may enable formation of various matching video questions using names, occupations, hobbies, areas and relation, as illustrated in FIG. 10.

As mentioned in the exemplary embodiments (described later), the present inventors have ascertained, using the present invention, a correlation meaningfully similar to the existing language memory test (SVLT: Seoul Verbal Learning Test) as a result of test on actual Alzheimer's patient and can distinguish a difference in response to Beta amyloid positive/negative without recourse to influence of user's education and age differently from the existing simplified mental state examination (MMSE: Mini Mental State Examination), whereby an effect can be accomplished by the degree of user's nerve disorder being more accurately grasped.

Meantime, the present invention may further comprise: a user response receiver analyzing a user response received by the user response receiver and distinguishing the user in response to the analyzed user's response. For example, it is also possible to group users based on correct rates in the user responses. Furthermore, it is preferable that the user's correct rates be scored based on the received user responses. Furthermore, the user response receiver can also determine the degree of a user's dementia progress based on the scored points.

In addition, a VR system for diagnosis of nerve disorder according to another exemplary embodiment of the present invention may include the VR device, and may further comprise a server analyzing a user response received from a user response receiver of the VR device and classifying a user according to the analyzed user response.

That is, the present invention may be also implemented by a system including a separate server analyzing the user response in addition to the RV device.

Furthermore, a method for VR device for diagnosis of nerve disorder according to still another general exemplary embodiment of the present invention may comprise: providing a VR environment to a user through a display in response to a video; and receiving a user response relative to the video, wherein the video includes an introduction video including two or more characters, and a question video provided subsequent to the introduction video to include a question related to the characters.

Here, the provision of the VR environment may be implemented by an HMD (Head Mounted Display) including a display.

Furthermore, the receipt of user response may be implemented by a controller including a button part receiving a user response relative to the question video.

The present invention may be better appreciated by the following exemplary embodiments and the following exemplary embodiments are merely for an exemplary purpose and do not restrict the scope of protection restricted by the accompanying claims.

First Exemplary Embodiment: VR Test for Nerve Disorder Diagnosis (Social Event Memory Test: SEMT)

A test subject was allowed to solve questions using a computer after watching a VR photographed by a 360° camera using an HMD.

The introduction video was that, as illustrated in Table 1, a main character was positioned at a center of a table and six congratulating persons were seated at both sides of the main character, as in a birthday party. That is, the congratulating persons were made to respectively repeat own information twice, while continuing a normal conversation in the video.

The successive question video was formed as below in the order of a Free-recall video, a face recognition video and a place-matching video.

1. Free-recall [36 points]
   Instructed to recall the content of video
   Test on 6 items (name, occupation, hobby, relation, present, area)
2. Face-Recognition [18 points]: limited to 15 seconds
   Faces of actors (6 persons) and non-actors (12 persons), a total of 18 faces were randomly shown and instructed to response by way of 0/X about appearance/disappearance
3. Position-matching test [48 points]: limited to 20 seconds
   6-question multiple choice question
   faces, presents, accessories (pictures)
   names, occupations, hobbies, areas, relation (words)
4. a total points: 102 points First Comparative Example 1: SVLT (Seoul Verbal Learning Test)

The SVLT is a Seoul Verbal Learning Test previously developed by the inventor.

That is, the SVLT is that a user is requested to talk as whatever comes to the user's mind regardless of order while a total of 12 words (e.g., azalea, chopping board, rose of Sharon, fountain pen, dish, pen, forsythia, paper, dipper, lily, pot and eraser) being called.

To be more specific, the test was performed through the following Immediate recall, Recognition, and Delayed recall processes.

1. Immediate recall: repeated three times
   requested to say the words that come to mind while 12 words were called
   A total of three times repeated
2. Recognition: The subject was provided with words in the list and words not in the list, and instructed to answer by way of 0/X whether the words are the words previously provided.
3. Delayed recall: instructed to say all remembered words regardless of order among the words previously provided 30 minutes after other subjects were given to perform.

First Experimental Example: Correlation Result

A correlation analysis was made between SEMT according to the first exemplary embodiment and SVLT result according to the first comparative example. To be more specific, a correlation with the existing Mini Mental State Examination (MMSE), age, academic background or educational level was comparatively compared.

Figure 11:
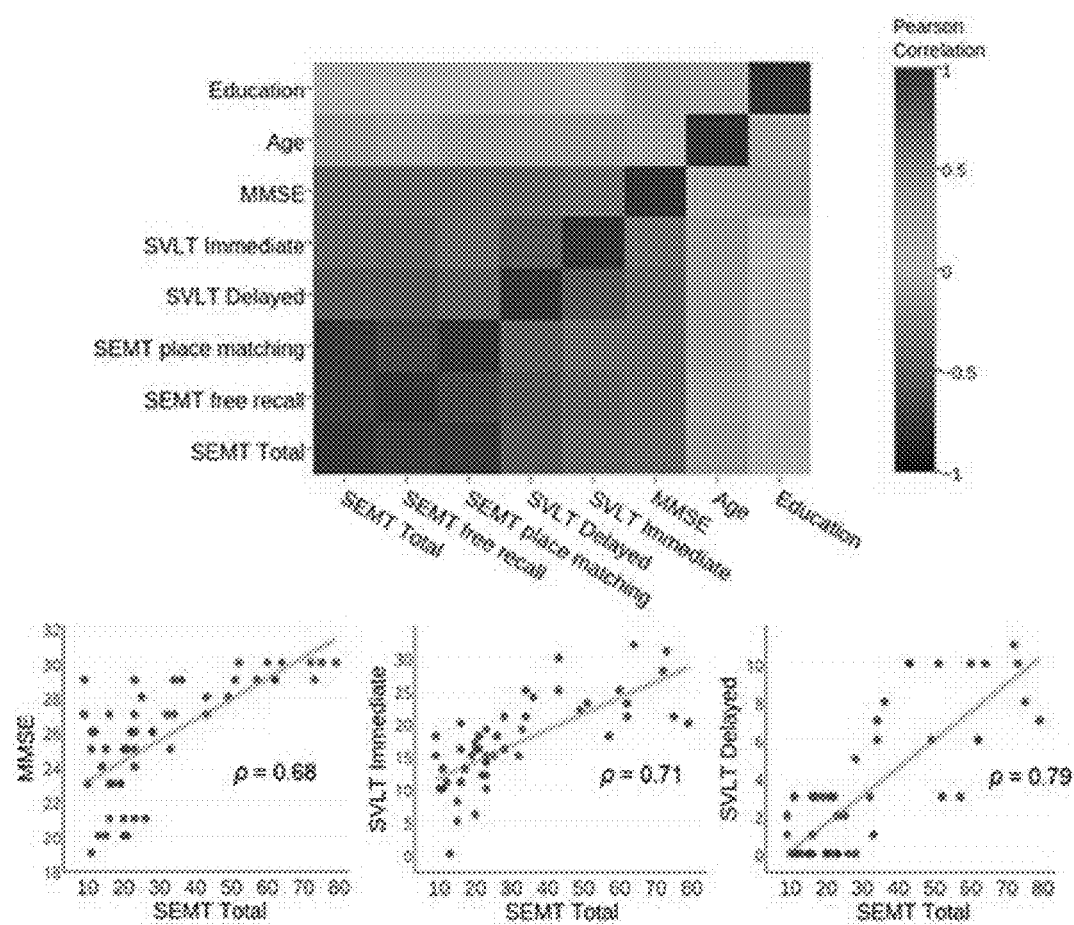
FIG. 11 is a graph illustrating a VR test for diagnosis of nerve disorder (SEMT: Social Event Memory Test) according to an exemplary embodiment of the present invention and illustrating, as a comparative example, a correlation result of an existing language memory test (Seoul Verbal Learning Test) and an existing simplified existing mental state examination (MMSE: Mini Mental State Examination).

FIG. 11 is a graph illustrating a VR test for diagnosis of nerve disorder (SEMT: Social Event Memory Test) according to an exemplary embodiment of the present invention and illustrating, as a comparative example, a correlation result of an existing language memory test (Seoul Verbal Learning Test) and an existing simplified existing mental state examination (MMSE: Mini Mental State Examination).

In the upper graph in FIG. 11, when r value is 1, it means a complete correlation, which is indicated in red color, and when r value is −1, it means a negative correlation, which is indicated in blue color, and when the r value is 0, it means that there is no correlation.

According to the above evaluation, an SEMT result showed a high correlation with the MMSE and SVLT, and inter alia, the Free-recall and the position-matching tests relative to associative ability and memory showed a high correlation.

Relatively, the face-Recognition test in the SEMT result is not high in correlation, and the face-Recognition test is related to the visual memory, and which is presumably due to a screen being unclear.

The SEMT result and the existing memory test SVLT have no relation with ages and educational background, and the MMSE, which is one of the neuro-psychological examinations, is greatly affected by educational level and is confirmed to be difficult in grasping the nerve disorder correctly.

Furthermore, in the bottom graph of FIG. 11, each dot shows that the SEMT of each subject and the SVLT point, which is the existing memory test, are made to be distributed, where when the p value is near to 1, it shows a positive relation.

Based on this result, the SEMT according to the present invention has generally shown a relatively high relation with the existing test method of MMSE and SVLT as well.

Second Experimental Example: Result of Analysis of Variance (ANOVA Result)

Tests were made on subjects of 13 normal persons (SMI), 29 MCI (Mild Cognitive Impairment) patients and 13 Alzheimer's patients (AD) using the STMT according to the first exemplary embodiment and SVLT according to the first comparative example, and then the Analysis of Variance (ANOVA) which is one of Multivariate statistical analyses was performed.

The result is as shown in the following Table 2.

TABLE 2

|  | SMI | MCI | AD | P |
|---|---|---|---|---|
| Age, years | 72.46 ± 3.86 | 75.48 ± 4.85 | 72.64 ± 6.79 | 0.13 |
| Education, years | 13.23 ± 3.85 | 12.92 ± 4.65 | 13.00 ± 3.80 | 0.98 |
| Gender |  |  |  |  |
| Female:Male | 8:5 | 14:11 | 6:8 | 0.596 |
| MMSE | 29.00 ± 1.08 | 25.72 ± 2.85 | 22.79 ± 2.39 | <.0001 |

TABLE 2-continued

| | SMI | MCI | AD | P |
|---|---|---|---|---|
| Domain score | | | | |
| Attention | 11 ± 2.80 | 9.24 ± 2.49 | 9.46 ± 2.22 | 0.1198 |
| Language | 24.62 ± 2.47 | 21.24 ± 3.91 | 22.31 ± 2.72 | 0.0172 |
| Visuospatial | 33.77 ± 1.74 | 29.62 ± 6.01 | 29.62 ± 7.35 | 0.0863 |
| Memory | 100.54 ± 12.27 | 47 ± 14.08 | 27.88 ± 8.92 | <.0001 |
| Frontal/ Executive | 57.69 ± 8.41 | 44.60 ± 12.70 | 39.38 ± 11.55 | 0.0005 |
| Total SEMT | 227.62 ± 24.18 | 151.70 ± 24.21 | 128.65 ± 20.47 | <.0001 |
| Free recall | 17.15 ± 5.90 | 4.00 ± 4.79 | 0.36 ± 0.50 | <.0001 |
| Recognition | 11.54 ± 2.33 | 11.08 ± 1.63 | 10.57 ± 2.06 | 0.41 |
| Place matching SVLT | 29.31 ± 10.22 | 10.40 ± 7.34 | 4.71 ± 3.45 | <.0001 |
| Immediate | 25.23 ± 3.92 | 15.79 ± 3.88 | 11.15 ± 4.86 | <.0001 |
| Delayed | 8.69 ± 1.75 | 2.04 ± 1.90 | 0.31 ± 0.85 | <.0001 |

* SMI(Subjective Memory Impairment): Normal person (person who lacks in recognition ability only according to subjective view point)
* MCI(Mild Cognitive Impairment): MCI patients
* AD(Alzheimer's Disease): Alzheimer's patients
* P: Significance(p-value)value, and when the p-value is lower than 0.0001, it is determined that there is a significance.
* Domain score: point of each domain of Seoul Neuro-psychological Screening Battery, SNSB) for diagnosis of dementia As illustrated in the above Table 2, the significance (p-value) of genders, ages and educational levels of subjects (gender) is significantly higher over 0.001, such that it was revealed that there is no big difference among the normal persons (SMI), MCI patients and Alzheimer's patients.

In contrast, the total points of Language, Memory and Frontal/execution in the scores of the existing Neuro-psychological tests of MMSE, SVLT and SNSB domain showed a significant difference for each test subject.

Particularly, the SEMT according to the present invention has shown a significant difference for each subject in the free-recall and place matching tests except for the recognition, whereby it can be confirmed that distinction of each patient group was possible.

Third Experimental Example: Classification Result by Machine Learning Method

The Classification performance and the Diagnostics performance were certified by learning the SEMT result scores (total scores: 102 points) according to the first Exemplary embodiment on 10 normal persons (SCI), 28 MCI patients, and 11 Alzheimer's patients (AD) using the machine learning method of SVM (Support Vector Machine).

That is, it was verified whether four groups of (SCI, aMCI(-), aMCI(+), AD) had been well classified using the scores of SEMT.

FIGS. 12A and 12B are graphs of a PC (Principal Component) result certifying whether four groups (SCI, aMCI(-), aMCI(+), AD) are well classified by a classifier using scores of SEMT according to an exemplary embodiment of the present invention.

FIGS. 12A and 12B are results where patient groups of same data are classified by two different PCs (Principal Components), where FIG. 12A is a linear kernel, and FIG. 12B is a radial kernel. The figures in FIGS. 12A and 12B illustrate groups belonged by the actual data. ○ shows SMI, □ indicates MCI(-), ∆ illustrates MCI(+), and ◇ shows AD. Furthermore, the color shows a result predicted by the classifier. The color of red is a result predicted by SMI, blue shows a result predicted by MCI(-), green indicates a result predicted by MCI(+), and yellow indicates a result predicted by AD.

According to the above data, it was confirmed that FIG. 12B (radial kernel) classifies the patient groups better than FIG. 12A (linear kernel), and hereinafter, patient groups were classified using the radial kernel.

The following Table 3 shows a classification performance result in a case where learning was made with the SEMT result scores according to the first Exemplary embodiment for subject, ages and educational background.

TABLE 3

| | Sensitivity (%) | Specificity (%) | PPV (%) | NPV (%) |
|---|---|---|---|---|
| SMI | 94.12 | 66.67 | 85.71 | 84.21 |
| | (0.76) | (0.85) | (0.56) | (0.86) |
| MCI- | 95.12 | 45.45 | 71.43 | 86.67 |
| | (0.85) | (0.80) | (0.98) | (0.97) |
| MCI+ | 93.94 | 68.42 | 86.67 | 83.78 |
| | (0.79) | (0.68) | (0.90) | (0.83) |
| AD | 93.75 | 70.00 | 87.50 | 83.33 |
| | (0.86) | (0.70) | (0.80) | (0.96) |

As illustrated in Table 3, the accuracy that classifies normal persons (SCI) was confirmed to reach 94.12% and the accuracy that classifies the AD was confirmed to reach 93.75% as a result of SEMT result scores of subjects and as a result of classifying the normal persons (SCI), the MCI and the AD using ages and educational background.

Furthermore, the accuracy to classify even the positive and negative of MCI patients (MCI) was confirmed to reach 95.12% and 93.94% respectively.

Fourth Experimental Example: Amyloid Positive/Negative Classification Result by Regression Method The Amyloid PET video was photographed for subjects of 13 normal persons (SCI), 25 MCI patients (MCI) and 14 Alzheimer's patients (AD), and 22 Amyloid negatives and 30 Amyloid positives classified thereby were experimented.

The SEMT result scores (total scores: 102 points) according to the first exemplary embodiment were predicted by Regression method of Rogistic regression model in terms of a probability value between 0 and 1 about presence and absence of Amyloid deposition. The Rogistic regression model was transformed to variables of infinite numbers in order to perform an approach method similar to the linear regression model.

The result thereof is as shown in FIG. 13 in which • shows PET positive patient groups, ∆ shows PET negative patient groups, and as the green color deepens, the regression models were diagnosed by PET negative, and as the red deepens, the regression models were diagnosed by the PET negative.

According to the above method, it was confirmed that the regression model classified the PET result of 50 persons except for 2 persons.

Meantime, the importance in making a fitting model is how the model is simplified. When a model goes complex and goes more complex, it may be possible to explain a large part of data, but the forecast on new data becomes far deteriorated, which is called an overfitting.

TABLE 4

Output for fitting model

| Model | DF | −Log Likelihood | Chi-square | P > Chi |
|---|---|---|---|---|
| Difference | 4 | 26.36 | 52.71 | <.0001 |
| Full | | 7.29 | | |
| Reduced | | 33.65 | | |
| R-squared (U) | 0.78 | | | |
| AIC | 25.95 | | | |

Lack of Fit

| Model | DF | −Log Likelihood | Chi-square | P > Chi |
|---|---|---|---|---|
| Full | 36 | 7.29 | 14.59 | 0.9994 |
| Saturated | 40 | 0.001 | | |
| Difference | 4 | 7.29 | | |

Likelihood Ratio Statistics

| Term | DF | L-R Chi square | P > Chi |
|---|---|---|---|
| SEMT total | 1 | 24.70 | <.0001 |
| SEMT total*SEMT total | 1 | 8.82 | 0.0030 |
| SEMT total*SEMT free recall | 1 | 9.38 | 0.0022 |
| SEMT free recall*SEMT free recall | 1 | 5.21 | 0.0225 |

*Main effect: Only one variable used
*Interaction effect: Interaction between two variables used
*Quadric effect: multiplication of two variables or interaction of squared values used The "output for fitting model" in the above Table 4 was to observe whether it is a simple model, whose p value of SEMT model was shown to be smaller than 0.001, which explains that the SEMT model is a sufficiently simple model.

The result of "Lack of Fit" was to observe whether the overfitting was made, which is shown to be 0.9994 and has a value near to 1, and explains a result that the SEMT model according to the present invention was not over-fitted.

The inventors have taken into consideration the main effect, interaction effect and quadric effect in the process of seeking an optimal model, and results of the Likelihood Ratio Statistics in the last of Table 4 could determine whether the coefficients of models are significant, and indicated that all showed meaningful, less than 0.05 p values, and explained that the SEMT models according to the present invention are meaningful optimal models.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A virtual reality (VR) system for diagnosis of nerve disorder, the system comprising:
   a display part providing a user with a VR environment that includes video images; and
   a user response controller receiving a user response to the video images, wherein the video images include images in an introduction video, and images in a question video provided subsequent to the introduction video to include an inquiry related to the introduction video, wherein the introduction video is a birthday party video including one or more main characters and two or more congratulating persons.

2. The VR system of claim 1, wherein the introduction video includes content in which the congratulating persons introduce in sequence information selected from a group consisting of own name, an occupation, a hobby, relation with the one or more main characters, a present and a living area.

3. The VR system of claim 1, wherein the congratulating persons in the introduction video have one or more identifiers selected from a group consisting of different genders, ages, accessories and clothes colors.

4. The VR system of claim 1, wherein the question video includes one or more videos including a recall video recalling the introduction video, a recognition video testing a memory of a face of the congratulating persons, and a matching video testing a memory relative to characteristics of the congratulating persons.

5. The VR system of claim 4, wherein the question video includes, in sequence, the recall video, the recognition video and the matching video.

6. The VR system of claim 4, wherein the recall video includes a questionnaire having questions about image or text content selected from a group consisting of an image or explanation designating one person from the congratulating persons, name of the designated person, occupations and hobbies of the congratulating persons, and relations of the congratulating persons with the one or more main characters, a present and a living area.

7. The VR system of claim 4, wherein the recognition video includes a face photograph of one person of the congratulating persons and a face photograph of a person who is not one of the congratulating persons.

8. The VR system of claim 4, wherein the recognition video includes, in a random order, a face photograph of one person of the congratulating persons and a face photograph of a person who is not one of the congratulating persons, where the face photograph of one person of the congratulating persons and the face photograph of a person who is not one of the congratulating persons are mutually distinguished.

9. The VR system of claim 4, wherein the matching video includes: a questionnaire having questions about image or text content selected from a group consisting of an image or explanation designating one person from the congratulating persons, a face, a name of the designated person, an occupation, a hobby, and a relation of the designated person with the one or main characters, a present and a living area; and one or more candidate answers selected from a group consisting of a face, a name, a hobby of a congratulating person, a relation of the congratulating person with the one or more main characters, a present and a living area.

10. A virtual reality (VR) system for diagnosis of nerve disorder,
    the system comprising:
    a display part providing a user with a VR environment that includes video images depicting social interactions among multiple persons; and
    a user response controller receiving a user response to the video images, wherein the video images include images in an introduction video, and images in a question video provided subsequent to the introduction video to include an inquiry related to the introduction video, wherein the introduction video is a birthday party video including one main character sitting at a table and six congratulating persons sitting around the main character.

* * * * *